United States Patent [19]
Kross

[11] Patent Number: 5,651,977
[45] Date of Patent: Jul. 29, 1997

[54] ADHERENT DISINFECTING COMPOSITIONS AND METHODS RELATING THERETO

[75] Inventor: Robert D. Kross, Bellmore, N.Y.

[73] Assignee: Alcide Corporation, Redmond, Wash.

[21] Appl. No.: 356,068

[22] Filed: Dec. 14, 1994

[51] Int. Cl.[6] ............... A01N 25/26; A01N 25/28; A61K 47/30
[52] U.S. Cl. ............................. 424/419; 514/772.3
[58] Field of Search ..................... 424/405, 407, 424/409, 419; 514/772.3

[56] References Cited

U.S. PATENT DOCUMENTS

| | | | |
|---|---|---|---|
| Re. 31,779 | 12/1984 | Alliger | 252/187 |
| 4,330,531 | 5/1982 | Alliger | 424/149 |
| 4,574,084 | 3/1986 | Berger | 424/128 |
| 4,891,216 | 1/1990 | Kross et al. | 424/28 |
| 4,956,184 | 9/1990 | Kross | 424/661 |
| 4,986,990 | 1/1991 | Davidson et al. | 424/665 |
| 5,100,652 | 3/1992 | Kross et al. | 424/53 |
| 5,185,161 | 2/1993 | Davidson et al. | 424/665 |
| 5,384,134 | 1/1995 | Kross et al. | 424/661 |
| 5,407,656 | 4/1995 | Roozdar | 423/477 |

*Primary Examiner*—Carlos A. Azpuru
*Attorney, Agent, or Firm*—Seed and Berry LLP

[57] ABSTRACT

Disinfecting compositions directed to the prevention of microbial infections are disclosed. The disinfecting compositions comprise a protic acid, a metal chlorite and a gelling agent which, when combined, provide an effective adherent matrix that acts as a disinfectant barrier for preventing transmission and propagation of microbial infections. The gelling agent includes at least 15% polyacrylamide. The compositions of this invention may be used as teat disinfectants, specifically for use in the dairy industry.

22 Claims, No Drawings

ADHERENT DISINFECTING COMPOSITIONS AND METHODS RELATING THERETO

TECHNICAL FIELD

This invention relates generally to disinfecting compositions for preventing microbial infections and, more particularly, to an adherent matrix for preventing transmission and propagation of bacterial infections in dairy cows.

BACKGROUND OF THE INVENTION

Bacterial infections affect a wide variety of animals (including humans), threatening their health and safety. For example, mastitis is a highly infectious bacterial infection affecting mammalian mammary glands. It is the most common, and the most costly, disease affecting dairy cows. Mastitis exists in two forms: "clinical," characterized by visually detectable alterations in milk and mammary gland, and "subclinical," where the infection is not directly evident by visual inspection. It has been estimated that at least one-half of the cows in the United States have mastiffs, and most of these infections are subclinical.

Many bacterial pathogens can cause mastitis, including *Strep. agalactiae, Staph. aureus, Strep. uberis, Strep. dysgalactiae, E. coli, P. aeruginosa* and Klebsiella species. Of these pathogens, *Strep. agalactiae* and *Staph. aureus* are associated with infections that arise primarily from contaminated milking equipment. Such infections are known as "contagious mastitis." The other mastiffs infections, known as "environmental mastiffs," primarily result from pathogens that contact the teat during the inter-milking period. These pathogens may be transferred from wind-borne matter, bedding material or ground contaminants, such as soil and manure, that contact the udder when the animal lies down. In all cases, the route of transmission of the pathogen to the inner gland is through the teat orifice.

To prevent mastitis, a variety of disinfecting teat dips have been developed. These disinfectants include iodophors, quaternary ammonium compounds, chlorhexidine, sodium hypochlorite, hydrogen peroxide, organic acids (e.g., capric, lactic, lauric), dodecylbenzene sulfonic acid (DDBSA), and chlorous acid. Several of these materials are very effective in limiting the transmission of contagious mastiffs by destroying the pathogens that contact the teat during, and immediately subsequent to, the milking operation. However, these teat dips do not have sufficient longevity to protect the teat from bacteria that contact the udder during the 8 to 12 hour inter-milking period, particularly in inclement weather and when the animal lies down.

A few longer-lasting protective compositions have been developed that reduce the incidence of environmental mastitis, but these compositions have inherent practical problems in both application and maintenance. For example, a non-germicidal acrylic latex teat dip, which dries as a protective film over the teat end and remains intact until the following milking, significantly reduces the possibility of acquiring certain infections. However, other infections may be fostered by its application, since bacteria tend to propagate in the moist region between the skin and such latex coatings. This can irritate the dermal layer and act as a conduit for the transfer of organisms to the teat orifice. Furthermore, the acrylic latex dip is inconvenient for dairy herders who must physically strip the latex from each teat prior to milking the animal. Despite the addition of germicides to alleviate the skin irritation, the acrylic latex dip has not proven to be commercially viable since inconvenience, incomplete action, and expense have remained prevalent and insurmountable problems.

A more successful composition for preventing mastitis is disclosed in U.S. Pat. No. 4,891,216. That patent is directed to a disinfecting composition in which longevity is achieved using a gelling agent formed from the polymerization of the monomer 2-acrylamido-2-methylpropane sulfonic acid ("polysulfonic acid"). This polysulfonic acid gelling agent is compatible with the metastable chlorous acid disinfecting system of U.S. Pat. No. 4,986,990, and forms a protective film over the teat end which limits the passage of contaminating environmental pathogens into the teat during the inter-milking period. This composition has been proven effective in field studies and is widely accepted by consumers for prevention of mastitis, and is sold under the name UDDER-GOLD (Alcide Corporation, Redmond, Wash.).

However, in spite of the many positive attributes of the disinfecting composition of U.S. Pat. No. 4,891,216, the strong affinity of the polysulfonic acid gelling agent to the dermal layer has proven problematic. Specifically, the polysulfonic acid film has a tendency to form a stubborn solid matrix at the teat end, especially when teat dip residues from prior applications have not been thoroughly washed off. Thus, after a series of successive post-milking applications accompanied by only partial removal of the residual film, the dairy herder is faced with a hard deposit at the teat end. Physical removal of the deposit can result in skin irritation and possibly removal of dermal tissue. The resulting sore areas and lesions cause significant discomfort during milking, particularly when vacuum milkers are used. In addition, when the polysulfonic acid gelling agent is combined with a metal chlorite (which, in combination with a suitable acid, generates the metastable chlorous acid disinfecting system), a high level of salts is produced. Such salts are potentially irritating to the teat skin when the solution dries to a hyperosmotic state.

Furthermore, manufacture of the disinfecting composition of U.S. Pat. No. 4,891,216 is complicated by the use of the polysulfonic acid gelling agent. Polysulfonic acid is commercially available only as a highly viscous aqueous solution (ca. 16% solids) with a $pH \leq 1$ (e.g., HSP-1180 from Henkel Corporation). As a result, manufacture of the disinfecting composition requires a preheating step to soften the polysulfonic acid, as well as high pressure to transfer the aqueous polymer to a mixing container. In addition, the polysulfonic acid polymer is difficult to use in the protic acid component of the disinfecting composition. Because of the high acidity of the polysulfonic acid polymer, it is difficult to precisely adjust the pH of a partially neutralized solution of polysulfonic acid and a protic acid so that the pH of the final composition is reproducible. Such predictability is required for uniformity of action since the concentration of chlorous acid in the disinfecting composition is critically dependent on the pH. The irreproducibility of pH when polysulfonic acid is used as the gelling agent substantially increases the cost of manufacture, and ultimately, the finished product.

Thus, there is a need in the art for a suitable disinfecting composition which will surmount the problems identified above. More specifically, there is a need in the art for a long-lasting disinfecting composition which will adhere to surfaces in an acceptable manner, that is easy to handle and manufacture, and that provides a readily-removable antimicrobial protective layer. The present invention fulfills these needs, and provides further related advantages.

SUMMARY OF THE INVENTION

In brief, this invention is directed to an adherent disinfecting composition for preventing microbial infections, as well as methods related to the use thereof for disinfecting substrate surfaces, including the skin of warm-blooded animals. The disinfecting composition comprises a protic acid, a metal chlorite, and a gelling agent of which at least about 15% by weight is polyacrylamide. Optionally, the disinfecting composition further comprises a humectant, a preservative and/or a dye. In a preferred embodiment, the substrate surface is the teat of a dairy cow, and a composition of this invention is applied to the teat resulting in the formation of an adherent matrix which disinfects and protects the teat from microbial infection. These and other aspects of this invention will become evident upon reference to the following detailed description.

DETAILED DESCRIPTION OF THE INVENTION

This invention is generally directed to an adherent disinfecting composition suitable for protecting against microbial infection. The disinfecting composition is applied to a substrate surface where it forms an "adherent matrix," which is a film or gel on the substrate surface that actively protects against microbial infection.

In the context of the present invention, the term "disinfecting composition" refers to a composition (prior to application to the substrate surface and the formation of the adherent matrix) comprising a protic acid, a metal chlorite and a gelling agent. The term "protic acid" is defined in greater detail below. A "metal chlorite" refers to alkali metal chlorites and alkaline earth metal chlorites, and includes so-called "stabilized chlorine dioxide" products that contain an alkali metal chlorite or an alkaline earth metal chlorite. The term "gelling agent" refers to a composition which, when combined with the other components of the disinfecting composition, increases the gelatinous quality or viscosity of the disinfecting composition and/or the adherent matrix; and the term "humectant" refers to a composition added as a softening agent which attracts moisture to the skin, aiding in skin hydration. The term "preservative" refers to a composition added to the protic acid component to prevent deterioration of the protic acid component.

The disinfecting composition of this invention may be provided in multiple phases. In one embodiment, the disinfecting composition is provided in three phases: a "protic acid solution" (which is an aqueous protic acid composition), a metal chlorite (in the form of a powder or an aqueous solution) and a gelling agent. In a preferred embodiment, the disinfecting composition is provided in two phases. The first phase comprises the protic acid. This phase may be a protic acid solution or a "protic acid gel," which is an aqueous composition comprising a protic acid and gelling agent. The second phase comprises the metal chlorite. If the first phase does not contain all of the gelling agent in the disinfecting composition, the second phase may additionally comprise some or all of the gelling agent. An aqueous phase that contains both metal chlorite and gelling agent is referred to as a "metal chlorite gel." In this two-phase system, all of the gelling agent in the disinfecting composition is provided in one or both of the phases.

Regardless of the form in which the gelling agent is provided, the total amount of gelling agent in the disinfecting composition generally ranges from about 0.5% to about 5.0%, preferably from about 1.0% to about 4.0%, and more preferably from about 1.25% to about 3.0% by weight of the disinfecting composition.

The gelling agent of this invention is chosen to provide exceptional stability and other beneficial properties to the adherent matrix. To this end, the gelling agent is stable for a long period of time in the alkaline metal chlorite gel, and for at least 8–24 hours in the acidic disinfecting composition. Thus, the gelling agent possesses the unusual property of maintaining its viscosity in both alkaline and acidic chlorite conditions.

Most compounds commonly employed as gelling agents do not possess the stability necessary for use in the practice of this invention. For example, although polyacrylic acid polymers (e.g., "carbopols") will maintain their viscosity in the alkaline oxidizing environment of chlorite solutions, these polymers lose much of their viscosity when the alkaline system (associated with $—COO^- Na^+$ groups on the polymer) converts to acidic conditions after contact with the protic acid components. Similarly, polymers susceptible to oxidative cleavage are not stable in the disinfecting composition. As a result, polymers derived from sugars, such as carrageenan (a polygalactan), ethyl-, methyl-, hydroxyethyl-, methyl hydroxyethyl- and methyl hydroxypropyl cellulose, guar gum (a galactose/mannose polymer) and many naturally occurring polymers do not provide the desired stability, despite the fact that such materials may maintain their viscosity under both acid and alkaline conditions. Synthetic polymers derived from poly(alkylene oxide) chains (e.g., polyethylene oxide family) are also subject to such oxidative degradation, and therefore do not confer the desired stability. While these and other polymers may be present in the disinfecting composition, the amount of such additional polymers is maintained at a level such that they do not significantly detract from the viscosity of the disinfecting composition and the adherence of the protective barrier. Preferably, such polymers are present only in the protic acid component.

Of the numerous gelling agents commercially available, it has been surprisingly found that, in addition to the polysulfonic acid disclosed in U.S. Pat. No. 4,891,216, only polyacrylamide is suitable in the practice of this invention. More specifically, the polyacrylamide of the present invention has the following formula:

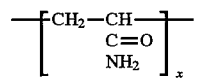

wherein X has a value such that the molecular weight is from about 1,000,000 to 20,000,000, preferably from about 2,500,000 to 10,000,000.

In the practice of this invention, between 15% and 100% of the gelling agent used to formulate the disinfecting composition must be polyacrylamide. Within this range, the amount of polyacrylamide may be varied, as described in more detail below, to alter the characteristics of the disinfecting composition and adherent matrix for specific applications. In a preferred embodiment, substantially all of the gelling agent that is not polyacrylamide is polysulfonic acid, or a suitable sulfonate salt thereof. The preparation of such compounds is disclosed and described in U.S. Pat. No. 4,891,216, which is incorporated herein by reference.

The protic acid component of the disinfecting composition may be any acid or mixture of acids capable of reducing the pH of the disinfecting composition to below about 6. Protic acids include organic acids, such as alpha-hydroxy acids of the general formula:

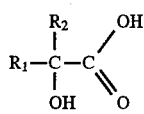

wherein $R_1$ and $R_2$ are independently selected from the group consisting of hydrogen, methyl, —$CH_2COOH$, —$CH_2OH$, —CHOHCOOH and —$C_6H_5$. In a preferred embodiment, the protic acid is an organic acid having a pK ranging from about 2.8 to about 4.2; and more preferably from about 3.0 to about 4.0. Typical organic acids include citric, malic, tartaric, glycolic, lactic, and mandelic. Alternatively, the protic acid may be an inorganic acid having a pK ranging from about 0 to about 2.2, such as sulfuric, hydrochloric or phosphoric acid.

Those of ordinary skill in the art will recognize that the concentration of protic acid in the disinfecting composition will vary depending on the strength of the protic acid. Organic acids will generally be present in an amount ranging from about 0.05% to about 5% by weight of the disinfecting composition. Stronger inorganic acids will generally be present in an amount ranging from about 0.005% to about 2% by weight of the disinfecting composition. In either case, the amount of protic acid in the disinfecting composition is sufficient to lower the pH of the disinfecting composition to below about 6, preferably from about 2 to about 5, and more preferably from about 2.5 to about 4.

In the practice of this invention, the protic acid may be provided as a protic acid solution or in the form of a protic acid gel, which comprises a protic acid and a gelling agent. In either case, the amount of protic acid in the solution or gel is sufficient to render the pH of the protic acid solution or gel generally less than about 5.5, typically from about 2.0 to about 4.5, and preferably from about 2.2 to about 4.0.

In the case of a protic acid gel, the gelling agent comprises one or more compounds that increase the viscosity of the gel. The gelling agent is generally present in amounts up to about 10%, typically up to about 4.0%, and preferably from about 0.5% to about 3.0% of the protic acid gel by weight. In a preferred embodiment, at least 50% of the gelling agent in the protic acid gel is polyacrylamide.

Optionally, the protic acid solution or gel additionally comprises one or more of the following: a humectant, a preservative and/or a dye. The optional humectant portion of the protic acid solution or gel comprises any suitable humectant known in the art, including, by way of example, glycerin and sorbitol. A humectant is a hydrophilic material that holds and attracts moisture to the skin, aiding in skin hydration. Humectants generally comprise up to 15.0%, typically from about 2.0% to 10.0%, and preferably from about 4.0% to 8.0% by weight of the protic acid solution or gel. The optional preservative portion of the protic acid solution or gel comprises any suitable preservative known in the art, including, by way of example, benzyl alcohol and sodium benzoate. Preservatives generally comprise up to 0.08%, typically from about 0.01% to 0.06%, and preferably from about 0.02% to 0.04% of the protic acid solution or gel. The optional dye may be any suitable dye known in the art including, by way of example, FD&C Yellow: #5.

The metal chlorite component of the disinfecting composition may be any water-soluble chlorite. Typical water-soluble chlorites include alkali metal chlorites and alkaline earth metal chlorites. Sodium chlorite and potassium chlorite are preferred, and sodium chlorite is particularly preferred.

In the practice of this invention, chlorous acid degrades to a series of cidal oxidants which, along with the chlorous acid, act as antimicrobial agents. The amount of chlorite ion that is in the form of chlorous acid varies, depending on the pH of the composition. When the protic acid is an organic acid, with a pK greater than about 2.8, the metal chlorite is present in an amount such that no more than about 15% of the chlorite ion is in the form of chlorous acid. When the protic acid is a strong acid, with a pK lower than about 2.8, the metal chlorite may be used in an amount such that the amount of chlorite ion in the form of chlorous acid is no more than about 25% of the total chlorite ion.

To maintain the above chlorous acid concentration, the chlorite is present in the disinfecting composition in an amount ranging from about 0.01% to about 1.0% by weight. Preferably, the chlorite is present in an amount ranging from about 0.01% to about 0.45%, and more preferably from about 0.1% to about 0.35%, by weight of the disinfecting composition.

The metal chlorite may be provided in powder form, in an aqueous solution or in the form of a metal chlorite gel. In the case of a metal chlorite gel, the gelling agent comprises one or more compounds that increase the viscosity of the gel, and the gelling agent is generally present in amounts up to about 10%, preferably from about 1.0% to about 5.0%, and more preferably from about 2.0% to about 4.0% by weight of the metal chlorite gel. In a preferred embodiment, at least 15% of the gelling agent in the metal chlorite gel is polyacrylamide and, more preferably, at least about 50% of the gelling agent in the metal chlorite gel is polyacrylamide.

The pH of the metal chlorite component should generally be maintained at greater than about 8, typically from about 8.5 to 12 and preferably from about 9 to 11. Suitable compounds for adjusting the pH of the metal chlorite component will be apparent to those skilled in the art, and include sodium hydroxide.

By varying the amount and composition of the gelling agent, the characteristics of the disinfecting composition and adherent matrix formed therefrom may be varied according to the desired antimicrobial application. Characteristics which may be varied include: drying time, tackiness, ease of removal with or without water, affinity to skin, viscosity, and membranous quality. In the practice of this invention, these characteristics are generally controlled by varying the amount and nature of the gelling agent and the ratio of polyacrylamide to polysulfonic acid.

For example, in some applications it may be advantageous to increase or decrease the viscosity of the disinfecting composition. The disinfecting composition will require a higher viscosity when the adherent matrix is to be formed on vertical surfaces, and when a thicker adherent matrix (which is less susceptible to erosion or rupture) or extended antimicrobial properties are desired. In contrast, the disinfecting composition will require a lower viscosity when the adherent matrix is to be formed on horizontal surfaces, when a thinner adherent matrix is desired, when gauze or cotton applicators are used, when faster evaporation is desired, and when there are nooks and crannies on the surface that must be filled.

To prepare a disinfecting composition with a lower viscosity, the amount of gelling agent may be decreased. A high level of gelling agent, such as about 5%, will generate a product that leaves a relatively large quantity of material on the substrate surface. The use of a lower level of gelling agent (less than about 1%) will result in a product that leaves lower amounts of material on the substrate surface. In determining how much gelling agent should be used, one of ordinary skill in the art will appreciate that the molecular weights of the gelling agents may be taken into account. A lesser amount of a long-chain polymer will impart the same viscosity to a solution as a greater amount of a shorter-chain polymer. In addition, equal-viscosity formulations prepared from long- and short-chain polymers will deposit adherent matrices having different thicknesses. The use of short-chain polymers will result in the deposition of a thicker adherent matrix.

For other applications it may be advantageous to increase or decrease the adherent affinity of the matrix to the skin. For use on udders of dairy cows, the composition should demonstrate sufficient affinity to the skin so that it is not readily removed by abrasion or contact, and yet is readily removable prior to milking. Generally, polysulfonic acid has a higher affinity for skin (polyacrylamide does not have as high affinity for skin, but forms a more cohesive film and dries more fully). Thus, a higher level of polysulfonic acid (e.g., greater than about 2% by weight of the total composition), and a lower level of polyacrylamide (e.g., less than about 0.75% by weight of the composition), will generate an adherent matrix with a relatively high affinity for the skin.

To prevent build-up after repeated use, it may be advantageous to increase the ease with which the adherent matrix may be removed with water. Ease of removability is enhanced by increasing the polyacrylamide component. A suitable formulation for application to allow removal with water, and yet protect mammalian teats from microbial infection, includes a composition in which about 50% of the gelling agent in the metal chlorite gel is polyacrylamide in combination with a protic acid gel in which 100% of the gelling agent is polyacrylamide, where the total amount of gelling agent in the disinfecting composition ranges from about 0.5% to about 2.5%.

It may also be advantageous to generate a disinfecting composition that dries rapidly. Drying time of the disinfecting composition is important when the surface will be exposed to foreign material which may stick to the adherent matrix, or for cosmetic reasons. When altering this characteristic, temperature, which tends to enhance evaporation, and humidity, which tends to suppress evaporation and increase drying time, should be taken into account. In general, increasing the ratio of polyacrylamide to polysulfonic acid decreases the drying time because of the lower affinity of polyacrylamide for water. Typical ratios of polyacrylamide to polysulfonic acid for rapidly drying disinfecting compositions range from about 0.5:1 to about 5:1, and preferably from about 1:1 to about 3:1.

When the disinfecting composition of this invention is provided in two phases, the protic acid solution or gel and the metal chlorite solution or gel are mixed in suitable ratios to generate the chlorous acid, and the disinfecting composition is then applied to the surface to be disinfected. Preferably, the two phases are combined in approximately equal parts. More preferably, the disinfecting composition is mixed immediately prior to application.

In one aspect of the present invention, the disinfecting composition may be applied to mammalian teats. The composition may be applied by any one of several means, including dipping, from one of a series of commercially available dip cups, or spraying from a nozzle suitably adjusted to dispense a gelled formulation. Although the effective amount may vary, generally 0.5 to 2.0 grams of disinfecting composition is sufficient. A more viscous formulation ($\geq 1000$ cps) will generally deposit closer to 2.0 grams per teat.

The present invention is illustrated by the following examples, which are to be regarded as illustrative rather than restrictive. Unless otherwise noted, all parts and percentages in the examples, as well as the specification and claims, are by weight.

EXAMPLES

Example 1

This example illustrates the use of a representative disinfecting composition of the present invention as a teat dip for application to cow udders, where the resulting adherent matrix has moderate adherence, and is relatively easy to remove from the skin of the teat.

A protic acid gel is prepared by mixing the following ingredients:

| Polyacrylamide | 2.00% |
| Lactic acid | 2.64% |
| Sodium benzoate | 0.04% |
| Poloxamer 188 | 0.40% |
| FD&C Yellow #5 | 0.30% |
| Water | q.s. |

A metal chlorite gel is prepared by mixing the following ingredients:

| Polyacrylamide | 2.00% |
| Triton X-100 | 0.45% |
| Sodium chlorite | 0.64% |
| Titanium dioxide | 0.01% |
| Sodium hydroxide | to pH 11 |
| Water | q.s. |

The two gels are blended in approximately equal amounts, preferably just prior to application. The resulting gel is applied to the cow teat, forming a solid shield around the teat upon drying. The adherent matrix (resulting from evaporation of the water component) forms a protective barrier over the teat end which is readily removed by rinsing the teat with water immediately prior to milking.

Example 2

This example illustrates the use of a representative disinfecting composition of the present invention as a teat dip for application to cow udders, where the resulting adherent matrix has a significant degree of adherence to the skin of the teat but can be readily removed by vigorous washing.

A protic acid gel is prepared by mixing the following ingredients:

| Malic acid | 3.00% |
| Natrosol 250MR | 1.00% |
| Isopropyl alcohol | 2.00% |
| Sodium benzoate | 0.04% |
| Poloxamer 188 | 0.40% |
| FD&C Yellow #5 | 0.30% |
| Water | q.s. |

A metal chlorite gel is prepared by mixing the following ingredients:

| Polyacrylamide | 0.50% |
| Polysulfonic acid, 16% solution | 15.00% |
| NaOH, 1N | 15.00% |
| Triton X-100 | 0.45% |
| Sodium chlorite | 0.64% |
| Titanium dioxide | 0.01% |
| Water | q.s. |

The two gels are blended in approximately equal amounts, and applied as in Example 1. The adherent matrix (resulting from evaporation of the water) is resistant to removal by erosion and moisture, even in inclement weather, but may be removed by vigorous washing.

Example 3

This example illustrates the use of a representative disinfecting composition of the present invention as a teat dip for application to cow udders, where the resulting adherent matrix has maximum ease of removability from the skin.

A protic acid gel is prepared as described in Example 2, and blended in equal amounts with a metal chlorite gel that is prepared as described in Example 1. After application to cow teats, the mixture dries to create an adherent matrix over the teat ends which shows moderate adherence to the teat, yet can be adequately removed during normal pre-milking washing of the udder so that there is little tendency for dried residues to build up and lead to irritation.

Example 4

This example illustrates the use of a representative disinfecting composition of the present invention as a teat dip for application to cow udders, where the resulting adherent matrix provides a good balance of adherence to teat skin and ease of removability.

A protic acid gel is prepared by mixing the following ingredients:

| | |
|---|---|
| Polyacrylamide | 1.00% |
| Lactic acid | 2.64% |
| Sodiium benzoate | 0.04% |
| Poloxamer 188 | 0.40% |
| FD&C Yellow #5 | 0.30% |
| Water | q.s. |

The metal chlorite gel is prepared by mixing the following ingredients:

| | |
|---|---|
| Polyacrylamide | 1.00% |
| Polysulfonic acid, 16% solution | 6.25% |
| Triton X-100 | 0.45% |
| Sodium chlorite | 0.64% |
| Titanium dioxide | 0.01% |
| Sodium hydroxide | to pH 11 |
| Water | q.s. |

The two gels are blended in approximately equal amounts, preferably just prior to application. The resulting gel is applied to the cow teat, forming a solid shield around the teat upon drying. The adherent matrix (resulting from evaporation of the water component) forms a protective barrier over the teat end which provides good adherence to the teat, along with ease of removability.

Example 5

This example illustrates, for the purpose of comparison, the properties of a composition that employs polymer thickeners as gelling agents for the metal chlorite gel, where the gelling agent does not include polyacrylamide.

Example 1 is repeated, but hydroxyethyl cellulose is used at the same 2% level in place of the polyacrylamide for the metal chlorite gel. This gel is not stable for an acceptable period of time, since the cellulose gum depolymerizes and loses viscosity. In addition, when the metal chlorite gel is combined with the protic acid gel, the cellulose gum is more rapidly further depolymerized through oxidation by the chlorine dioxide created by the admixture. The use of a hydroxyethyl cellulose thickener for the metal chlorite gel in this manner results in a composition which shows a viscosity loss of more than 10% in three months, which is unacceptable for a commercial product.

From the foregoing, it will be evident that although specific embodiments of the invention have been described herein for the purpose of illustrating the invention, various modifications may be made without deviating from the spirit and scope of the invention.

I claim:

1. A composition for disinfecting a substrate and providing a protective antimicrobial barrier, comprising:
   (a) a protic acid;
   (b) a metal chlorite; and
   (c) a gelling agent in an amount ranging from about 0.5% to about 5.0% by weight of the composition, wherein the gelling agent comprises 15% to 100% by weight polyacrylamide.

2. The composition of claim 1 wherein the gelling agent is present in an amount ranging from about 1.0% to about 4.0% by weight of the composition.

3. The composition of claim 1 wherein the gelling agent is present in an amount ranging from about 1.25% to about 3.0% by weight of the composition.

4. The composition of claim 1 wherein the protic acid is an organic acid present in an amount ranging from about 0.05% to about 5% by weight of the composition.

5. The composition of claim 1 wherein the protic acid is an inorganic acid present in an amount ranging from 0.005% to about 2% by weight of the composition.

6. The composition of claim 1 wherein the metal chlorite is present in an amount ranging from about 0.01% to about 1.0% by weight of the composition.

7. The composition of claim 1 wherein the polyacrylamide is present in the gelling agent in an amount ranging from 50% to 100% by weight.

8. The composition of claim 1 wherein the polyacrylamide has a molecular weight ranging from about 1,000,000 to about 20,000,000.

9. The composition of claim 1 wherein the polyacrylamide has a molecular weight ranging from about 2,500,000 to about 10,000,000.

10. The composition of claim 1 wherein substantially all of the gelling agent that is not polyacrylamide is polysulfonic acid.

11. A composition for disinfecting a substrate and providing a protective antimicrobial barrier, comprising a first and second phase adapted to be mixed and applied so as to adhere to the substrate, the first phase comprising a protic acid and the second phase comprising a metal chlorite, wherein one or both of the first and second phases additionally comprise a gelling agent such that the total amount of the gelling agent ranges from about 0.5% to about 5.0% by weight of the composition, and wherein 15% to 100% by weight of the gelling agent is polyacrylamide.

12. The composition of claim 11 wherein the first phase comprises the gelling agent.

13. The composition of claim 11 wherein the second phase comprises the gelling agent.

14. The composition of claim 11 wherein the first and second phases comprise the gelling agent.

15. The composition of claim 11 wherein the gelling agent that is not polyacrylamide is polysulfonic acid.

16. The composition of claim 11 wherein the first phase comprises all or a portion of the gelling agent in an amount up to about 10% by weight of the first phase.

17. The composition of claim 11 wherein the first phase comprises all or a portion of the gelling agent in an amount ranging from about 0.5% to about 3.0%.

18. The composition of claim 11 wherein the second phase comprises all or a portion of the gelling agent in an amount up to about 10% by weight of the second phase.

19. The composition of claim 11 wherein the second phase comprises all or a portion of the gelling agent in an amount ranging from about 2.0% to about 4.0%.

20. A method for disinfecting a substrate, comprising applying to the substrate an effective amount of a composition comprising:

(a) a protic acid;

(b) a metal chlorite; and (c) a gelling agent in an amount ranging from about 0.5% to about 5.0% by weight of the composition, wherein the gelling agent comprises 15% to 100% by weight polyacrylamide.

21. The method of claim 20 wherein the substrate is a teat of a mammal.

22. The method of claim 20, further comprising the step of mixing a first phase and a second phase prior to applying the composition to the substrate, wherein the first phase comprises the protic acid and the second phase comprises the metal chlorite, and wherein the gelling agent is provided in one or both of the first and second phases.

* * * * *